(12) United States Patent
Parker

(10) Patent No.: US 6,343,224 B1
(45) Date of Patent: *Jan. 29, 2002

(54) REUSABLE PULSE OXIMETER PROBE AND DISPOSABLE BANDAGE APPARATUS

(75) Inventor: Brent Parker, Murrieta, CA (US)

(73) Assignee: Sensidyne, Inc., Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/417,898

(22) Filed: Oct. 14, 1999

Related U.S. Application Data

(63) Continuation-in-part of application No. 09/289,647, filed on Apr. 12, 1999, now Pat. No. 6,144,868.
(60) Provisional application No. 60/104,332, filed on Oct. 15, 1998.

(51) Int. Cl.[7] .................................................. A61B 5/00
(52) U.S. Cl. ....................................... 600/344; 600/310
(58) Field of Search ................................. 600/310, 322, 600/323, 340, 344

(56) References Cited

U.S. PATENT DOCUMENTS

| | | |
|---|---|---|
| 4,621,643 A | 11/1986 | New, Jr. et al. |
| 4,685,464 A | 8/1987 | Goldberger et al. |
| 4,700,708 A | 10/1987 | New, Jr. et al. |
| 4,830,014 A | 5/1989 | Goodman et al. |
| 5,090,410 A | 2/1992 | Saper et al. |
| 5,094,240 A | 3/1992 | Muz |
| 5,170,786 A | 12/1992 | Thomas et al. |
| 5,437,275 A * | 8/1995 | Amundsen et al. .......... 600/323 |
| 5,507,286 A | 4/1996 | Solenberger |
| 5,673,693 A | 10/1997 | Solenberger |
| 5,678,544 A | 10/1997 | DeLonzor et al. |
| 5,817,010 A | 10/1998 | Hibl ........................... 600/344 |
| RE36,000 E | 12/1998 | Swedlow et al. |
| 6,144,868 A * | 11/2000 | Parker ......................... 600/344 |

* cited by examiner

Primary Examiner—Eric F. Winakur
(74) Attorney, Agent, or Firm—Jim Zegeer

(57) ABSTRACT

A reusable pulse oximeter sensor and disposable bandage apparatus includes: a) a reusable pulse oximeter probe assembly with at least one light-emitting diode and one photocell detector wherein the detector and emitter are enclosed in plastic housings one housing having an aperture or radiation transparent window aligned with the emitter and the other housing having an aperture or radiation transparent window aligned with the detector; and b) a bandage strip having adhesive on at least a portion of at least one face thereof and at least two plastic receptacles mounted thereon, each receptacle having at least one aperture or radiation transparent window located therein; wherein the probe housings can matedly engage the bandage receptacles, and transmit and receive light through the apertures or radiation transparent windows of the mated housings and receptacles, and through the appendage of a patient.

15 Claims, 8 Drawing Sheets

REUSABLE PULSE OXIMETER PROBE AND DISPOSABLE BANDAGE APPARATUS

REFERENCE TO RELATED APPLICATION

This application is a continuation-in-part of patent application Ser. No. 09/289,647 filed Apr. 12, 1999 and entitled REUSABLE PULSE OXIMETER PROBE AND DISPOSABLE BANDAGE APPARATUS, now U.S. Pat. No. 6,144,868, which in turn is a nonprovisional application of provisional application Serial No. 60/104,332 filed Oct. 15, 1998.

BACKGROUND OF THE INVENTION

Heretofore the use of pulse oximeter probes has been limited to the use of a costly reusable probe, which is contaminated by use on a patient, or cheaper, single-use probes, which, in the aggregate, amount to a considerable expenditure for a health care institution. The present invention relates to a method of making and affixing a reusable probe to a patient by means of disposable bandage apparatus so that there is no contact between the costly, reusable portion of the probe and the patient. The contaminated bandage apparatus, which is relatively inexpensive, can then be discarded after single patient use and the probe can be reused with a new bandage apparatus. that process, the original adhesive material is removed from the original manufacturer's sensor. The sensor is then laminated in a plastic sheath and the entire sheath is then inserted into a transparent, adhesive-backed sleeve, which is then adhered to a patient. After use, the probe can then be extracted from the sleeve and inserted into a new sleeve for use on another patient.

There are certain disadvantages to this method. Firstly, it is difficult to insert the flexible laminated sensor into a long sleeve. Secondly, the thickness of a laminated sensor inside of a sleeve makes it difficult to bend around, and to stick properly to, a human appendage. Thirdly, transmission and reception of infrared light can be affected by extraneous light entering from the sides of the sleeve. And, Fourthly, there is some dispute as to the affect on infrared light transmission when passing through the sleeve and the adhesive material coupled thereto.

THE PRESENT INVENTION

The present invention not only solves the problems outlined above, but offers an alternative that is cheap to manufacture and easy to use.

In detail, the present invention is a method for improving the form and affixation method of a reusable pulse oximeter sensor. It comprises a reusable pulse oximeter probe with at least one light-emitting diode and one photocell detector wherein the emitter and detector are enclosed in plastic housings, one housing having an aperture or radiation transparent window aligned with the emitter, and the other housing having an aperture or radiation transparent window aligned with the detector. Also included is a disposable bandage apparatus which is a bandage strip having adhesive on at least a portion of at least one face thereof and at least two plastic receptacles mounted thereon, each receptacle having at least one aperture or radiation transparent window located therein. The probe housings can matedly engage the bandage receptacles and transmit and receive light through the apertures or radiation transparent windows of the mated housings and receptacles, and through the appendage of a patient. The apertures of the receptacles are large enough to accept the tubular protrusions of the housings for the purpose of concentric location and alignment of the housings to the receptacles and the proper transmission and reception of light therethrough. Sandwiched between the adhesive strip and the receptacles attached thereto, are translucent silicone windows or windows of another radiation transparent material for isolation of the reusable probe assembly from the patient. The bandage apparatus may be discarded after single patient use and the reusable probe may be used again on another patient in conjunction with another bandage apparatus. Additionally, the receptacles of the bandage apparatus may have a concave surface on one side thereof in order to seat conformably on a human digit, or they have a flat surface on at least one side thereof in order to attach conformably to a human foot, nose,or ear. The housings and receptacles also contain "mushroom hook" type hook and loop material for the purpose of adhering and detaching the housings to and from the receptacles. Additionally, the housings and receptacles have recessed areas for adhesion of the "mushroom hook" hook and loop material.

In another embodiment of the invention, the receptacle of the disposable bandage apparatus may be the mushroom hook material itself which may be attached directly to the adhesive strip for the selective engagement of the housings of the probe assembly.

Finally, and in the preferred embodiment of the invention, the light-emitting diode and photocell detector of the probe assembly may be mounted in modular housings with locking levers which can engage an indentation or slot in the receptacles and securely lock the housings into proper position within the receptacles, thus allowing the transmission and reception of infrared light through the mated housings and receptacles and through the appendage of a patient. In this embodiment, the silicone, or other radiation transparent windows, may be mounted against the skin of a patient, and may be used to secure the receptacles on the opposite side of the bandage strip. This is accomplished by the use of locking levers which are pushed through holes or slots in the bandage and engage the receptacles mounted on the opposite side of the bandage, thus sandwiching the bandage in between.

DESCRIPTION OF THE DRAWINGS

The above and other advantages of the invention will become more clear when considered with the following specification and accompanying drawings wherein.

DESCRIPTION OF THE REUSABLE PULSE OXIMETER SENSOR

Figure 1:
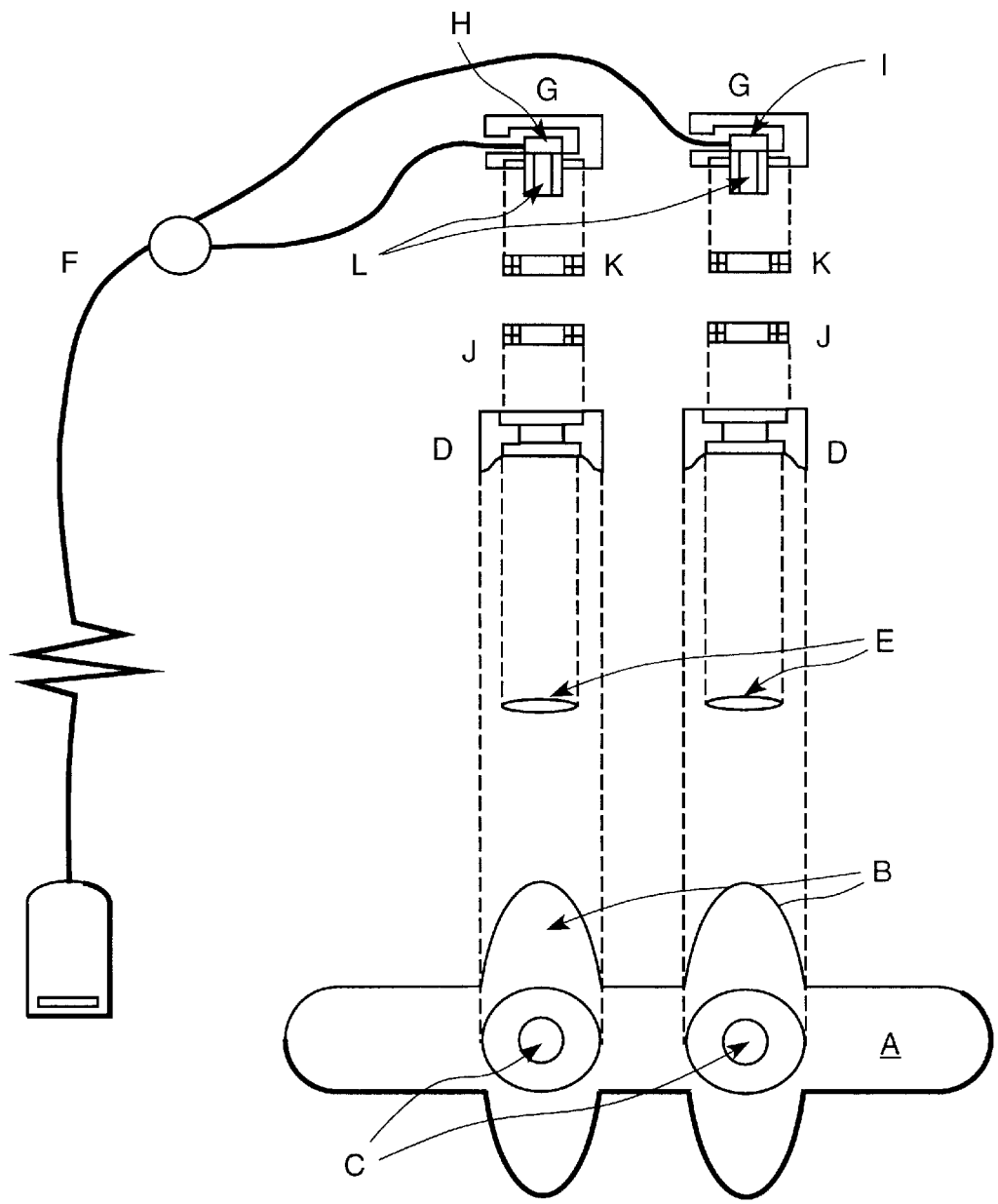
FIG. 1 is an exploded view of the reusable pulse oximeter probe and disposable bandage apparatus incorporating the invention.

The reusable pulse oximeter sensor constitutes a "Y" style pulse oximeter probe shown in FIG. 1, Item F. The probe incorporates two plastic housings shown as FIG. 1, Items G. The housings contain apertures or radiation transparent windows L therein. One housing contains the light-emitting diode of the probe, FIG. 1, item H, and other contains the photocell detector, FIG. 1, Item I. The emitter and detectors are aligned with the apertures or windows L of the housings in order to transmit and receive light through a human appendage.

Seated within a recessed area of each housing, and attached permanently thereto, is a "mushroom hook" adhesive-backed pad, FIG. 1, Item K. The purpose of these pads is to selectively engage the "mushroom hook" pads, FIG. 1, Items J, attached permanently to the plastic discs, FIG. 1, Items D, and to attach the reusable probe assembly to the Disposable Bandage Apparatus. The reusable pulse oximeter sensor is shown assembled as FIG. 2, Item A.

Figure 5:
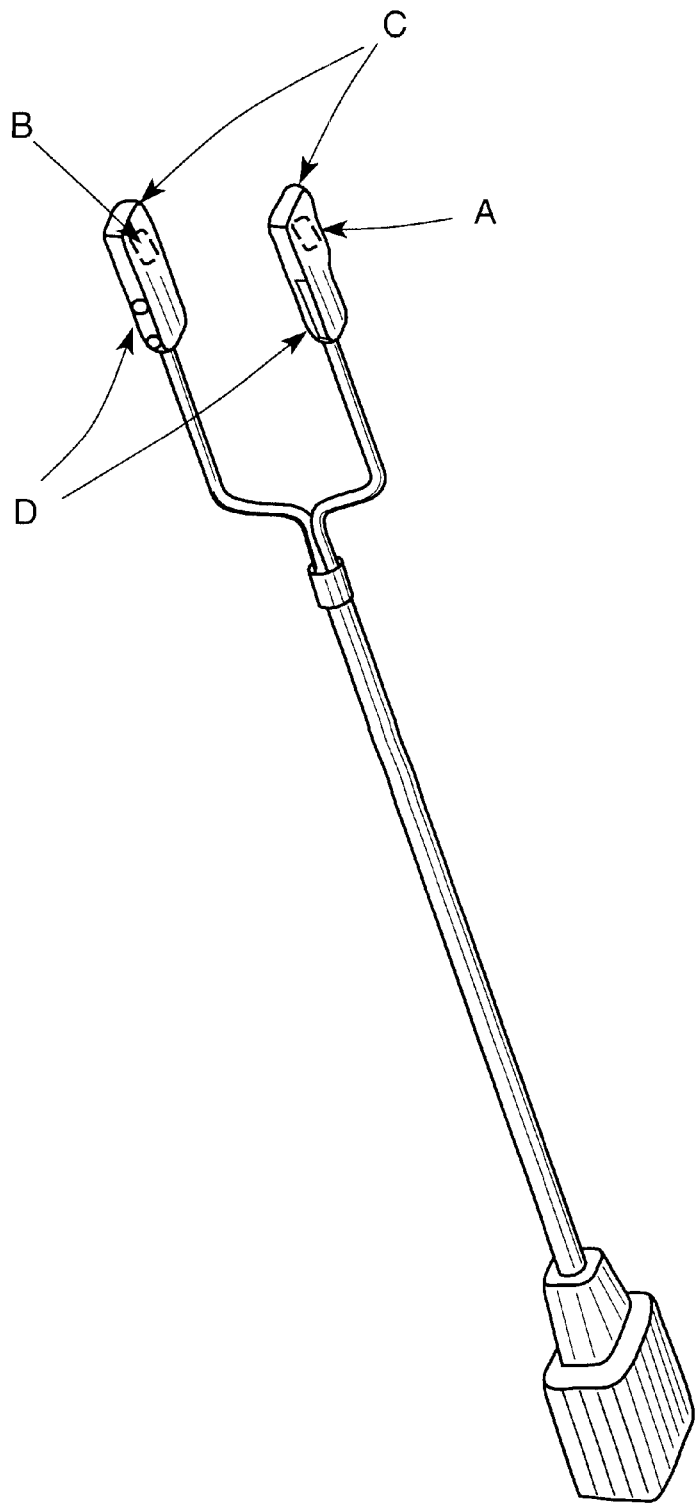
FIG. 5 illustrates an assembled view of the preferred embodiment of the reusable pulse oximeter sensor in which the light-emitting diode and photocell detector of the reusable probe are mounted in modular housings with locking levers.
Figure 6:
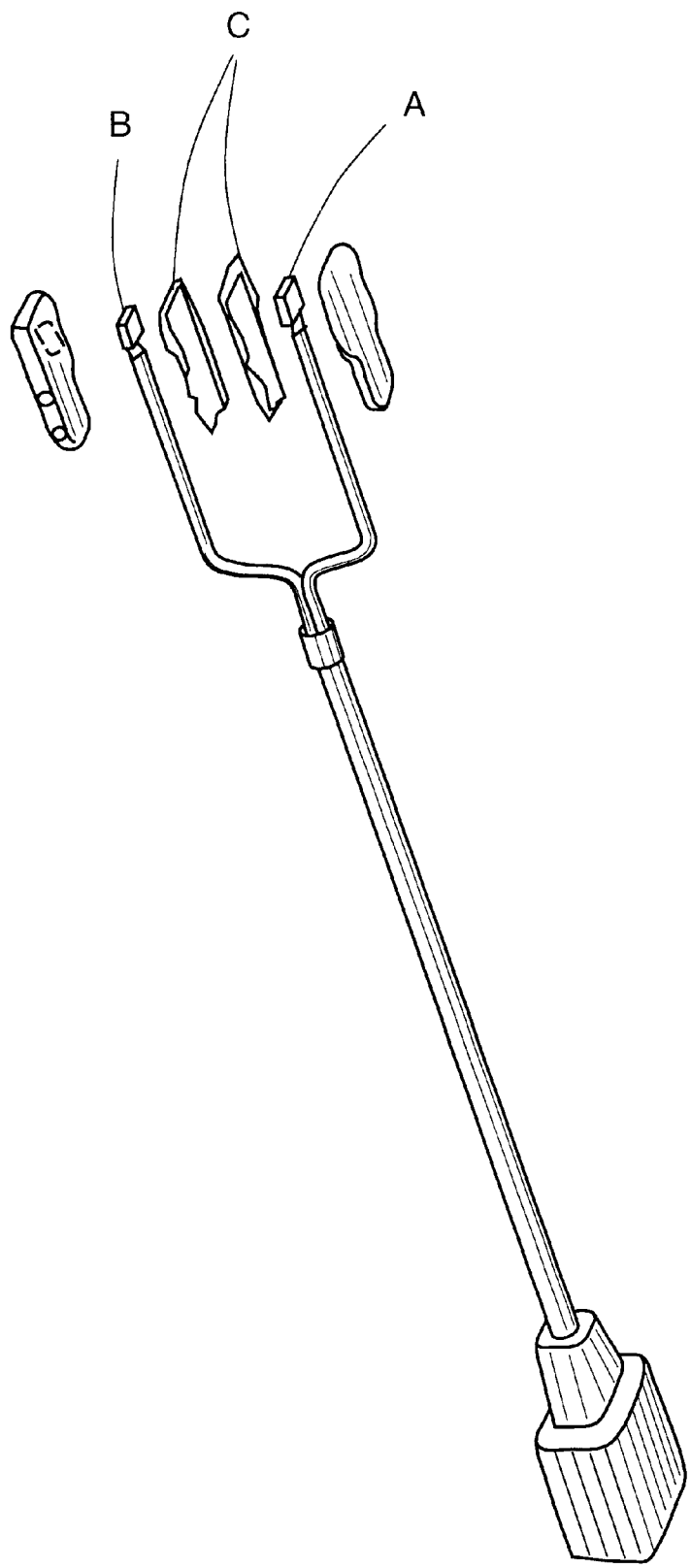
FIG. 6 illustrates an exploded view of the preferred embodiment of the reusable pulse oximeter sensor.

In the preferred embodiment of the reusable pulse oximeter sensor, the light-emitting diode (FIG. 5, Item A) and photocell detector (FIG. 5, Item B) of the probe assembly are housed in modular receptacles (FIG. 5, Items C) having locking levers (FIG. 5, Items D) for engaging the receptacles of the disposable bandage apparatus, and locking them into place. In this embodiment, the light-emitting diode (FIG. 6, Item A) and the photocell detector (FIG. 6, Item B( are sandwiched between interlocking receptacle halves, the bottom halves of which (FIG. 6, Items C) are made of a radiation transparent material.

DESCRIPTION OF THE DISPOSABLE BANDAGE APPARATUS

The components of the apparatus include an adhesive-backed strip, shown as FIG. 1, Item A, the strip A incorporating two oval protrusions B centered thereon and shown as FIG. 1. The strip also incorporates two apertures, centrally located within the oval protrusions, each aperture C having a diameter sufficient in size to accommodate the transmission and reception of light from a light-emitting diode and photocell detector of a pulse oximeter probe.

On top of the apertures C are seated two plastic discs, FIG. 1, Item D, each having a concave base designed to conform to the radius of a human digit, and an aperture of slightly larger diameter than the apertures in the adhesive backed planar strip. The plastic discs are affixed to the adhesive planar strip by means of a permanent adhesive.

Seated in a recessed area on top of each plastic disc is a "mushroom hook", adhesive backed pad shown as FIG. 1, Item J. The purpose of the "mushroom hook" pads is to selectively engage the "mushroom hook" pads attached to the probe, FIG. 1, Items K, and to attach the probe to the disposable bandage apparatus. Sandwiched between the two plastic discs and the planar adhesive strip are two translucent silicone windows, FIG. 1, Item E. The windows are designed to permit the passage of infrared light and yet prevent contact between probe and patient, and consequently, contamination of the reusable probe itself.

Figure 2:
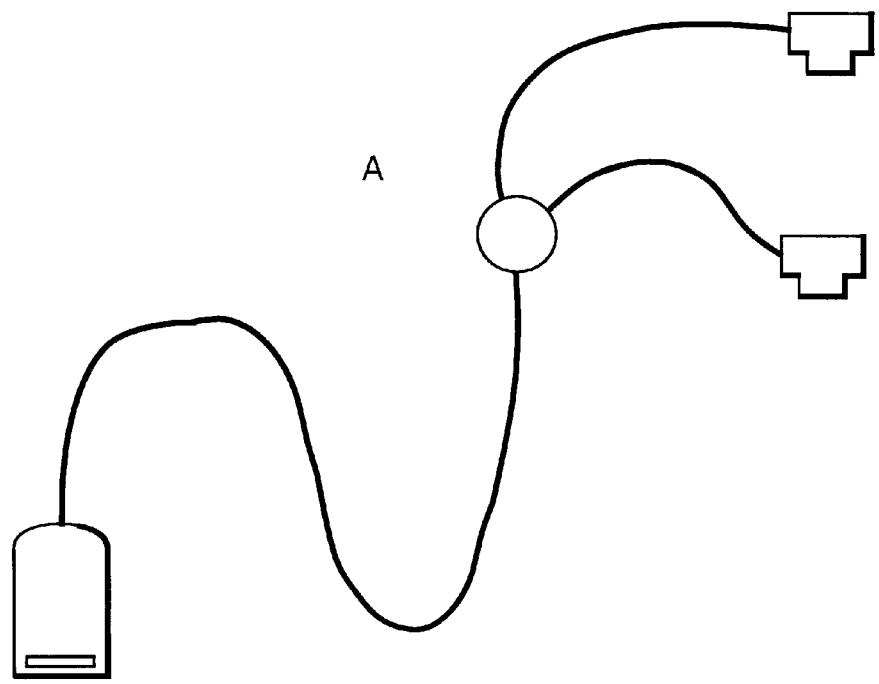
FIG. 2 is a view of the reusable pulse oximeter probe and disposable bandage apparatus shown individually as components of the invention.
Figure 2:
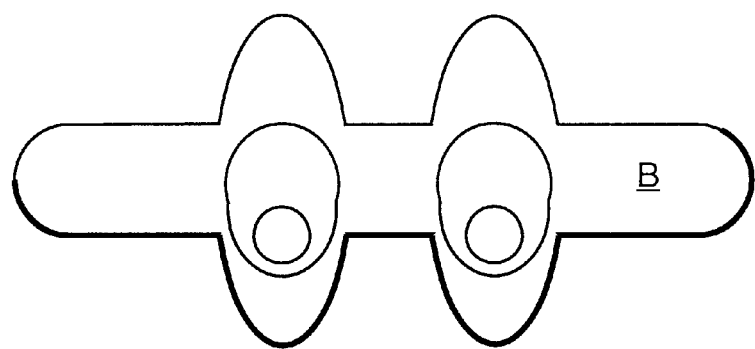

The above items constitute the disposable bandage apparatus of the invention, the apparatus being shown assembled as FIG. 2, Item B.

Figure 4:
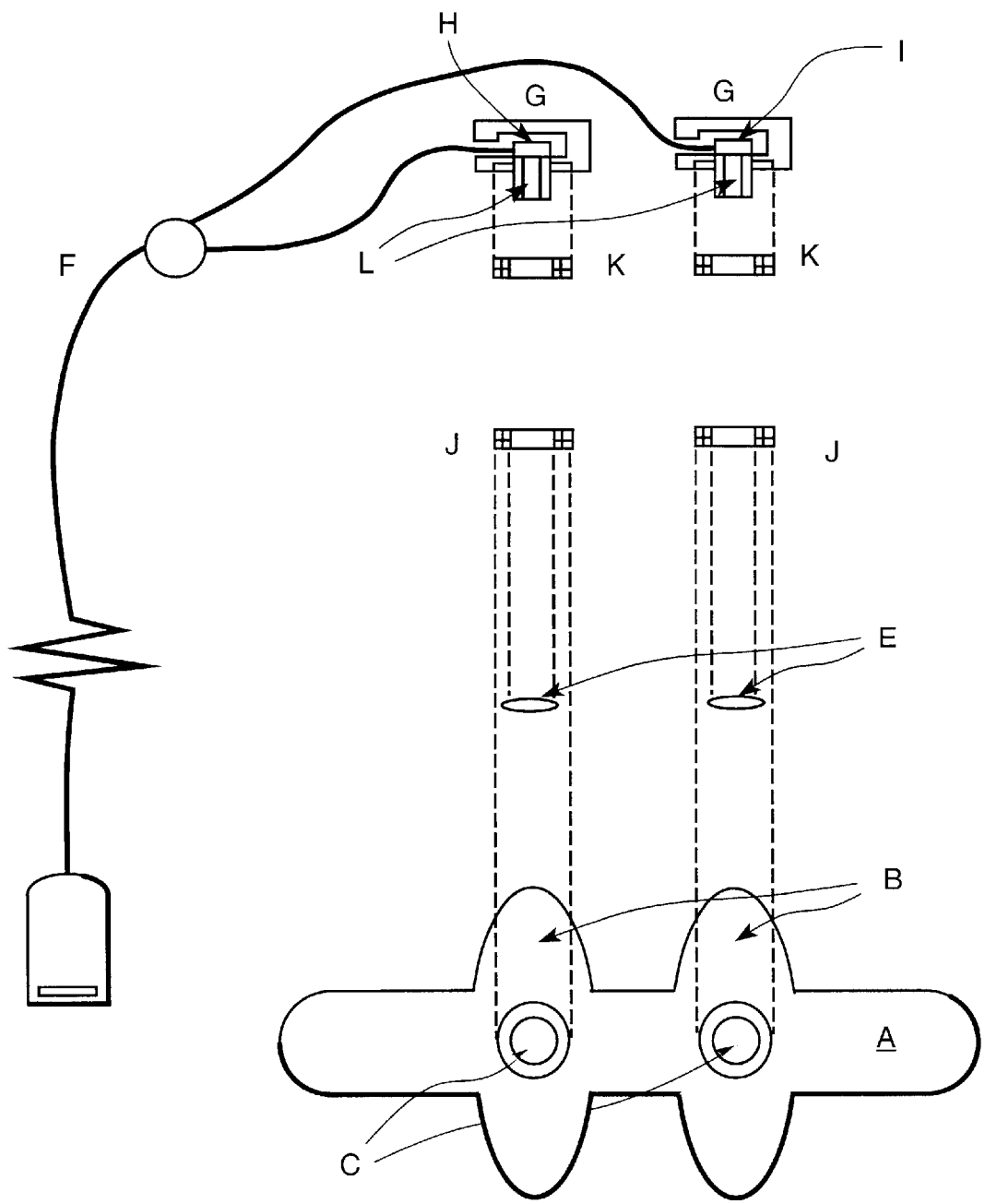
FIG. 4 illustrates an exploded view of another embodiment of the invention in which the "mushroom hook" material itself is used as the receptacle of the disposable bandage apparatus.

In another embodiment of the invention, the disposable bandage apparatus may be configured as in FIG. 4 of the drawings. FIG. 4 is an exploded view of the apparatus in which the "mushroom hook" pads of the bandage apparatus, FIG. 4, Items J, are bonded directly to the adhesive planar strip, FIG. 4, Item A, for the selective engagement of the "mushroom hook" pads of the probe, FIG. 4, Items K, the pads being attached permanently to the housings of the probe, FIG. 4, Items G.

Figure 7:
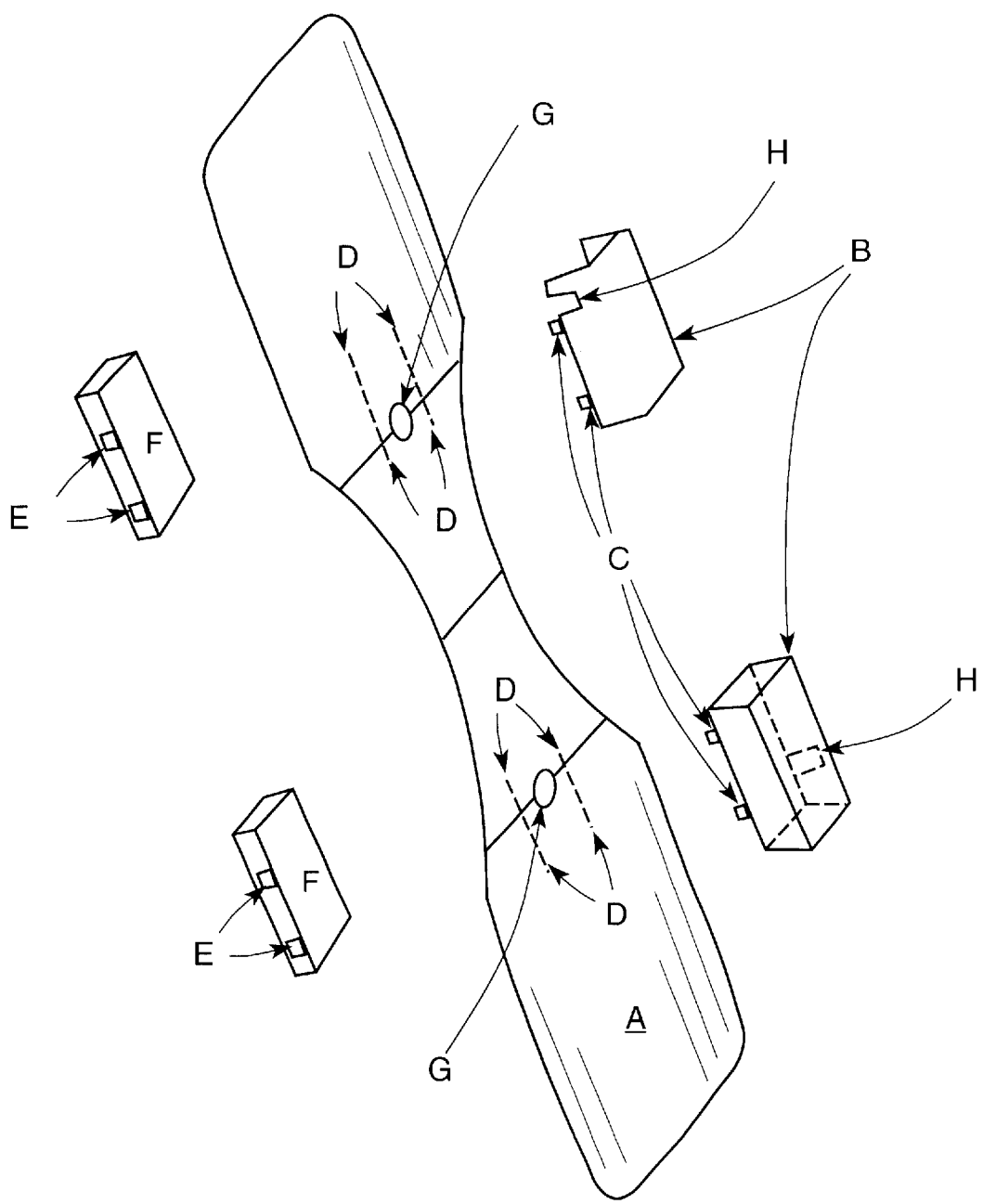
FIG. 7 illustrates an exploded view of the preferred embodiment of the bandage apparatus in which the receptacle tops incorporate a slot for engaging the locking levers of the modular probe housings, and wherein the radiation transparent windows are mounted on the opposite side of the bandage strip thus sandwiching and securing the bandage in between the two receptacle halves by means of locking levers.
Figure 8:
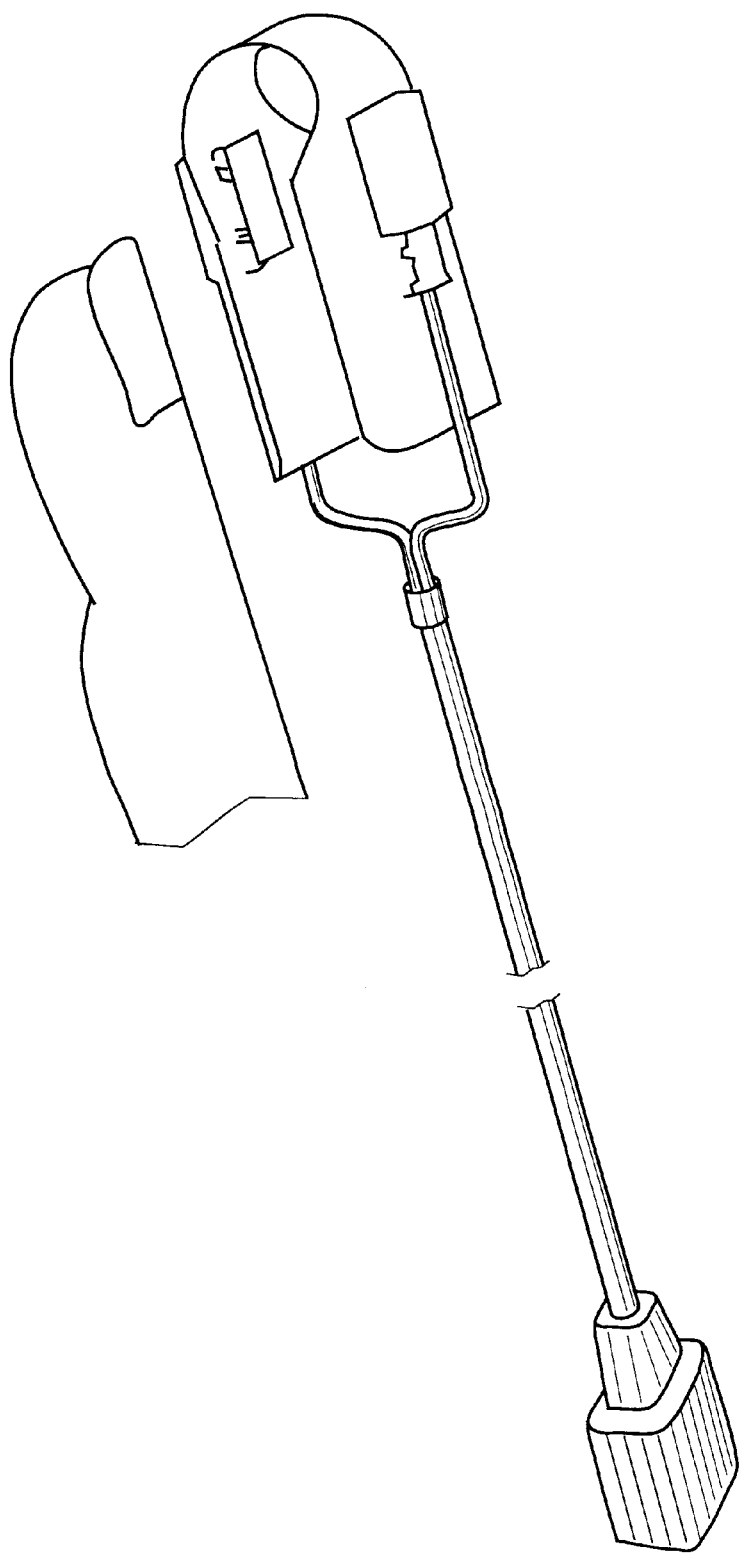
FIG. 8 illustrates the preferred embodiment of the invention as it would appear ready for use on a human digit.

In the preferred embodiment of the disposable bandage apparatus, the bandage strip (FIG. 7, Item A) is sandwiched between interlocking receptacle halves. The top halves of the receptacles (FIG. 7, Items B) contain locking levers (FIG. 7, Items C) that are pushed through slots cut in the bandage strip (FIG. 7, Items D) and lockingly engage indentations (FIG. 7, Items E) in the bottom halves of the receptacles (FIG. 7, Items F), thus sandwiching and locking the bandage in between. The bandage strip contains two apertures (FIG. 7, Items G) for the transmission and reception of light from the light-emitting diode and photocell detector of the pulse oximeter sensor which are encased in modular housings having locking levers (FIG. 5, Items D) wherein the levers engage slots in the receptacles (FIG. 7, Items H) thereby locking the housings into place within the receptacles. In addition, the bottom halves of the receptacles (FIG. 7, Items F) are of a radiation transparent material, thus allowing the light-emitting diode and photocell detector contained in the probe housings, when engage din the bandage receptacles, to transmit and receive light through the apertures of the bandage strip and through the radiation transparent material of the bottom halves of the receptacles, and through the appendage of a patient. The complete reusable pulse oximeter probe and bandage assembly is shown assembled and ready for use on a human digit in FIG. 8.

Other Fastening Means

As can be appreciated, there are many ways of fabricating the above components of the invention. The above description describes attachment of the reusable pulse oximeter sensor to the disposable bandage apparatus by way of a "mushroom hook" type hook and loop material and by the use of telephone type modular connectors and receptacles. In addition to this means, a number of other methods may be used including standard hook and loop material, "ring and groove" type snap-on connectors, "push and twist" type Luerlock connectors, and threaded flange type connectors.

Method of Use

Figure 3:
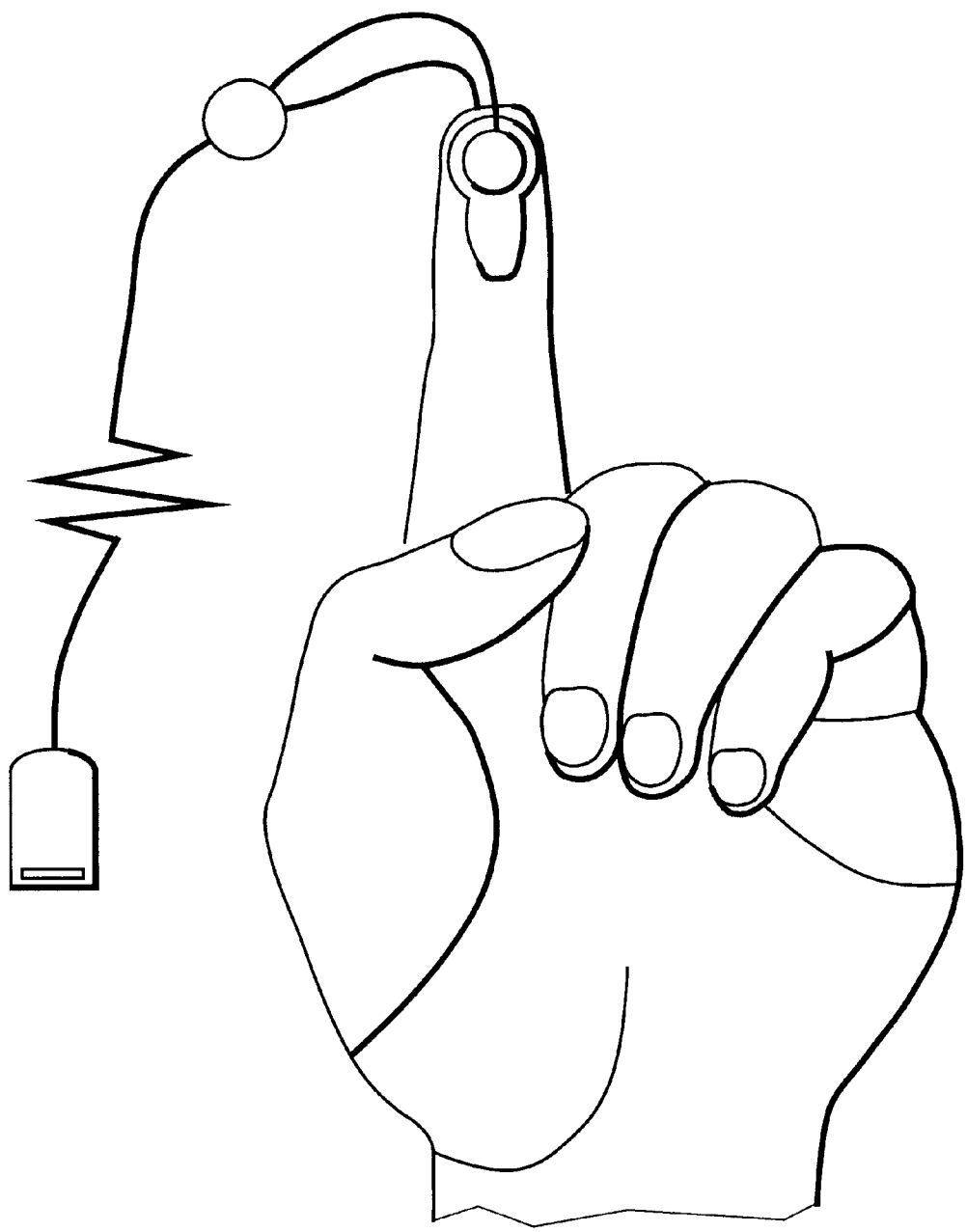
FIG. 3 illustrates the invention in use on a human finger or digit.

For use on each individual patient, the probe is affixed in the following manner:

Firstly, the backing is removed from the adhesive strip of the disposable bandage apparatus. One of the apertures of the apparatus is visually positioned on the center of the nail bed of the patient's appendage and one side of the adhesive strip and the oval protrusions are adhered to the patient's digit. The rest of the strip is then looped over the end of the patient's appendage, and the plastic disc is aligned so as to exactly oppose the plastic disc already attached to the other side of the digit. Once the disposable bandage apparatus has been properly adhered to the patient, the plastic housings of the probe assembly can be easily snapped into place on opposing sides of the digit. The entire assembled probe is shown as it would appear in use on a patient in FIG. 3.

For use with each patient, the modular probe and bandage assembly, which is the preferred embodiment of the invention, would be attached as follows:

Firstly, the backing is removed from the adhesive strip. The strip is then folded where indicated on the bandage and the strip is then adhered to opposing sides of the human digit. Once the bandage apparatus is in place, the housings of the probe are pushed into the receptacles and locked in place by means of the locking levers.

In all embodiments of the invention, when the probe is no longer required on the patient, the housings of the reusable probe are simply unsnapped from the disposable bandage apparatus, the bandage apparatus is thrown away, and the probe can then be reused on a new patient in conjunction with a new bandage apparatus.

ADVANTAGES OF THE PRESENT INVENTION

Current reusable pulse oximeter probes are either "clam shell" type clamping devices which can restrict circuit or "Y" type probes which are taped directly to the patient. Both types also come in direct contact with the patient's skin and bodily fluids and need sterilization after use. Because of the fact that these devices incorporate many surfaces and at times, porous materials, proper sterilization is very difficult. With the present invention there is no contact between the reusable probe and the skin or bodily fluids of the patient.

Disposable probes are very costly because of the fact that the cable, connectors and photodiodes are all disposed of after use. The present invention accomplishes the same goals as a disposable probe from a cleanliness standpoint, but since only the attachment apparatus is discarded after use, the cost is much less to a healthcare institution.

The present invention, with the concave shape of the plastic discs of the bandage apparatus, when backed by the adhesive strip, is extremely effective in preventing the entrance of extraneous light from the sides of the patient s digit. Current probes on the market, whether disposable or reusable, because of the nature of their shape and affixation means, have problems in dealing with extraneous light reception.

The present invention utilizes an easy snap-on, snap-off, or modular connector attachment means for attaching the probe to the disposable bandage apparatus. Probe-shield type devices available in the past not only required the modification of the original manufacturer's probe, but required the difficult procedure of inserting a flexible laminated probe into a sheath for each patient.

Probe-shield devices, because of the lamination process involved, raised some concern over the transmission and reception of infrared light through the laminating material. The present invention uses a silicone window for the isolation of the probe from the patient. Infrared light transmission and reception is not affected by passage through translucent silicone.

In these days of environmental consciousness, the annual waste generated from tens of millions of disposable probes is enormous. The present invention, if used in considerable numbers, would greatly reduce the amount of environmental waste generated by disposable pulse oximeter probes.

While the invention has been described in relation to preferred embodiments of the invention, it will be appreciated that other embodiments, adaptations and modifications of the invention will be apparent to those skilled in the art.

What is claimed is:

1. A disposable bandage apparatus for use with a reusable pulse oximeter sensor assembly having at least one light-emitting diode and one photocell detector wherein said detector and emitter are each enclosed in a male probe housing, respectively, one probe housing having an aperture or radiation transparent window aligned with said emitter and a second one of said probe housings having a radiation transparent window aligned with said detector, said bandage apparatus comprising a bandage strip having adhesive on at least a portion of at least one face thereof and two plastic female receptacles spacedly mounted thereon, each receptacle having at least one radiation transparent window located therein; wherein said male probe housings can matedly engage said female receptacles, and transmit and receive light through the apertures or radiation transparent windows of said housings and receptacles when mated, and through the appendage of a patient.

2. The disposable bandage apparatus of claim 1 wherein translucent silicone radiation transparent windows are sandwiched between said bandage strip and said receptacles attached thereto.

3. The disposable bandage apparatus of claim 1 wherein said female receptacles have a concave shape on one side thereof in order to seat conformably on a human digit.

4. The disposable bandage apparatus of claim 1 wherein said receptacles have a flat surface on at least one side thereof in order to seat conformably on a human ear, nose or foot.

5. The disposable bandage apparatus of claim 1 wherein the housings and receptacles contain "mushroom hook" type hook and loop material for the purpose of adhering and detaching said housings to and from said receptacles.

6. The disposable bandage apparatus of claim 5 wherein the housings and receptacles have recessed areas for adhesion of the "mushroom hook" hook and loop material.

7. The disposable bandage apparatus of claim 5 wherein the receptacles of said disposable bandage are the "mushroom hook" material itself.

8. The disposable bandage apparatus of claim 1 wherein the receptacles mounted thereon can matedly engage modular housings with locking levers, said receptacles having a notch, slot or indentation therein whereby at least a portion of said locking levers can lodge therein, thus locking and securing said housings to said receptacles.

9. The bandage apparatus of claim 1 wherein at least a portion of said plastic receptacles themselves constitute said radiation transparent windows.

10. A disposable oximeter mounting strip for use in oximetry, said mounting strip having first and second sides and a pair of radiation transparent windows, adhesive on said first side for attachment to an appendage of a patient, a removable backing strip adhered to said adhesive and a pair of modular female receptacle sockets mounted, in respective alignment with said pair of windows, on said second side for matedly and removably engaging a reusable modular pulse oximeter probe emitting diode and a reusable pulse oximeter probe photocell detector, respectively.

11. The mounting strip of claim 10 wherein each of said modular female receptacle sockets incorporates a locking lever for removably engaging said modular reusable pulse oximeter probe light emitting diode and photocell detector, respectively.

12. A method for the affixation of a reusable pulse oximeter sensor to the digit of a patient, comprising, providing a planar adhesive strip with at least two apertures therein, and two plastic receptacles mounted on top of said apertures, respectively, visually aligning on said digit of a patient by looking through a first of said apertures in order to position said first aperture over the nail bed of said patient's digit, then affixing said adhesive strip on the patient's digit prior to the engagement of the reusable probe in said plastic receptacles.

13. A disposable bandage apparatus for use with a reusable pulse oximeter sensor assembly having at least one light-emitting diode and at least one photocell detector wherein said detector and emitter are enclosed in, or mounted to, probe housings, one of said probe housings having at least one aperture or radiation transparent window aligned with said emitter and a second one of said probe housings having at least one aperture or radiation transparent window aligned with said detector, said bandage apparatus comprising at least one bandage strip having adhesive on at least a portion of at least one face thereof, and at least two plastic receptacles mounted thereon, each receptacle having at least one radiation transparent window located therein; wherein each of said probe housings can matedly engage at least one of said receptacles, and transmit and receive light through the apertures or radiation transparent windows of said housings and receptacles when mated, and through the appendage of a patient.

14. The disposable bandage apparatus of claim 13 wherein said receptacles have a concave shape on one side thereof in order to seat conformably on a human digit.

15. At least one disposable mounting strip for use in oximetry, said at least one mounting strip having first and second sides, and at least two radiation transparent windows located therein, adhesive on at least a portion of said first side for attachment to the appendage of a patient, at least one removable backing strip adhered to at least a portion of said adhesive, and at least two receptacles mounted on said second side, and in respective alignment with said at least two windows, said receptacles for matedly and removably engaging a reusable pulse oximeter probe light-emitting diode and a reusable pulse oximeter probe photocell detector respectively.

* * * * *